United States Patent [19]

Horwell et al.

[11] Patent Number: 4,906,655

[45] Date of Patent: Mar. 6, 1990

[54] NOVEL 1,2-CYCLOHEXYLAMINOARYL AMIDES USEFUL AS ANALGESIC AGENTS

[75] Inventors: David C. Horwell; David C. Rees, both of Cambridge, England

[73] Assignee: Warner-Lambert Company, Morris Plains, N.J.

[21] Appl. No.: 301,219

[22] Filed: Jan. 24, 1989

[51] Int. Cl.$^4$ .................. C07D 405/02; C07D 295/12; A61K 31/40
[52] U.S. Cl. .................................. 514/422; 514/428; 548/525; 548/528
[58] Field of Search ................ 548/525, 528; 514/422, 514/428

[56] References Cited

U.S. PATENT DOCUMENTS

| | | | |
|---|---|---|---|
| 4,145,435 | 3/1979 | Szmuszkovicz | 514/210 |
| 4,438,130 | 3/1984 | Kaplan . | |
| 4,463,013 | 7/1984 | Collins et al. . | |
| 4,656,182 | 4/1987 | Horwell . | |
| 4,738,981 | 4/1988 | Horwell | 548/525 |

Primary Examiner—Mukund J. Shah
Assistant Examiner—Frederick F. Tsung
Attorney, Agent, or Firm—Elizabeth M. Anderson

[57] ABSTRACT

Novel 1,2-cyclohexylaminoaryl amides useful as analgesic agents having very high kappa-opioid affinity and selectivity and potency and useful as analgesics, diuretics, antiinflammatory and psychotherapeutic agents are disclosed. Methods for making the compounds and pharmaceutical compositions containing them are also disclosed.

16 Claims, No Drawings

NOVEL 1,2-CYCLOHEXYLAMINOARYL AMIDES USEFUL AS ANALGESIC AGENTS

BACKGROUND OF THE INVENTION

The search for strong analgesics which also possess minimal potential for dependency has been among the highest priority efforts in pharmacological research. These research efforts have, to a great extent, involved chemical modifications of the opiate structure and the discovery of chemically novel compounds which possess morphine-like activity.

The concept of multiple opioid receptors has been supported by studies with nalorphine and a series of benzomorphans which display unusual pharmacological properties dissimilar from morphine, yet blocked by the opioid antagonists. [See, for example, W. R. Martin, et al., *J. Pharmacol. Exp. Ther.*, 197:517-531 (1976)].

The existence of multiple types of opioid receptors is of importance because it suggests the possibility of separating the desirable analgesic and psychotherapeutic effects of a drug compound from the undesirable abuse potential or habituating effect.

U.S. Pat. No. 4,145,435 describes certain 2-aminocycloaliphatic amide compounds as analgesic. In particular, trans-3,4-dichloro-N-methyl-N-[2-pyrrolidinyl)cyclohexyl]benzeneacetamide has been reported to possess selective kappa opioid agonist activity, and therefore to possess analgesic activity without attendant dependence liability. [See P. V. Vonvoigtlander, et al., *J. Pharmacol. Exp. Ther.*, 224:7-12 (1983)].

Recently, the diuretic effect of various opioid agonists and antagonists has been studied, and it has been shown that kappa agonists tend to increase urination, while mu agonists decreased urination. [See J. D. Leander, *J. Pharmacol. Exp. Ther.*, 227:35-41 (1983)]. These findings suggest that opioid agonists and antagonists also possess potential as diuretics.

U.S. Pat. No. 4,656,182 describes certain trans-1,2-diaminocyclohexyl amides useful as analgesics, diuretics, and psychotherapeutics.

U.S. Pat. No. 4,463,013 discloses certain oxygen substituted amino-cyclohexyl-benzeneacetamides as diuretics.

U.S. Pat. No. 4,438,130 discloses certain monooxa-, thiaspiro-cyclic-benzeneacetamide and benzamide compounds useful as analgesics.

SUMMARY OF THE INVENTION

One aspect of the present invention is a compound of formula

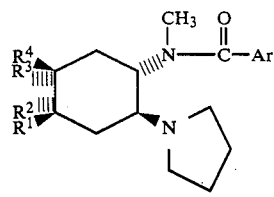

I and the pharmaceutically acceptable acid addition salt thereof wherein $R^1$, $R^2$, $R^3$, $R^4$, and Ar are as defined below.

Preferred compounds of the present invention are those of formula I wherein $R^1$, $R^2$, $R^3$, and $R^4$ are hydrogen.

Other preferred compounds of the present invention are those of formula I wherein one of $R^1$, $R^2$, $R^3$, and $R^4$ is —$OCH_3$ or wherein $R^1$ and $R^4$ are both —$OCH_3$.

Still other preferred compounds of the present invention are those of formula I wherein $R^1$ and $R^2$ are taken together to form

and $R^3$ and $R^4$ are both hydrogen.

Another aspect of the present invention is a compound of formula I wherein Ar is

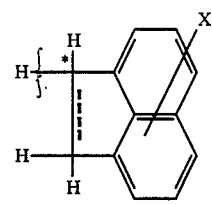

Ia wherein X may be hydrogen, fluorine, chlorine, alkyl of from one to six carbon atoms, or aryl. Preferably X is $NO_2$, Cl, Br, or alkyl or alkoxy from $C_1$-$C_6$. X may be attached to the ring shown in Ia at any one of the open positions. The asterisk indicates a chiral center, both enantiomers (isomers I and II) and the racemates are preferred.

The dotted line in Ia indicates that the $C_1$-$C_8$ bond may be unsaturated or saturated.

Another aspect of the present invention is a compound of formula I wherein Ar is

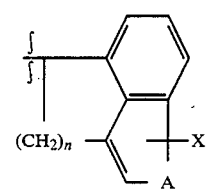

Ib

A = S or O only n = 2⟶4 only wherein n is an integer of from two to four and A is oxygen or sulfur. Preferably n is two and A is O or S. X is as above.

Another aspect of the present invention is a compound of formula I wherein Ar is

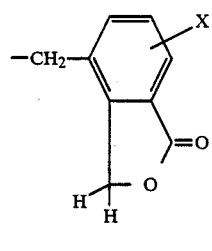

Ic or

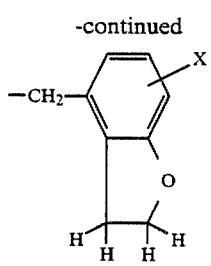

Id wherein X is hydrogen, fluorine, chlorine, alkyl of from one to six carbon atoms, or alkoxy. Preferably X is hydrogen, Cl, Br, $NO_2$, or alkyl or alkoxy from $C_1$-$C_6$. X may be attached to the ring at any one of the open positions.

Another aspect of the instant invention is a compound of formula I wherein Ar is

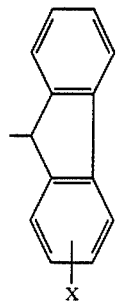

Ie wherein X is hydrogen, fluorine, chlorine, alkyl of from one to six carbon atoms, or aryl. Preferably X is hydrogen, Cl, Br, or $NO_2$. X may be attached to the ring at any open position.

Especially preferred compounds of the present invention are:

1,2-dihydro-N-methyl-N-[2-(1-pyrrolidinyl)cyclohexyl]-1-acenaphthylenecarboxamide, monohydrochloride (isomer I, mixture of (1α,2β) and (1β,2α) forms), 1,2-dihydro-N-methyl-N-[2-(1-pyrrolidinyl)cyclohexyl]-1-acenaphthylenecarboxamide, monohydrochloride (isomer II, mixture of (1α,2β) and (1β,2α) forms), N-[4,5-dimethoxyl-2-(1-pyrrolidinyl)cyclohexyl]-1,2-dihydro-N-methyl-1-acenaphthylenecarboxamide, monohydrochloride (isomer I, mixture of (1α,2β,4β,5β) and (1β,2α,4α,5α) forms), N-[4,5-dimethoxy-2-(1-pyrrolidinyl)cyclohexyl]-1,2-dihydro-N-methyl-1-acenaphthylenecarboxamide, monohydrochloride (isomer II, mixture of (1α,2β,4β,5β) and (1β,2α, 4α,5α) forms), 1,2-dihydro-N-methyl-N-[7-(1-pyrrolidinyl)-1-oxaspiro[4.5]dec-8-yl]-1-acenaphthylenecarboxamide, monohydrochloride (isomer I, (5α,7α,8β) form), and 1,2-dihydro-N-methyl-N-[7-(1-pyrrolidinyl)-1-[oxaspiro[4.5]dec-8-yl]-1-acenaphthylenecarboxamide, monohydrochloride (isomer II, (5α,7α,8β) form).

When Isomer I and Isomer II mean the two enantiomers of the 1-acenaphthene carboxylic acid.

Another aspect of the present invention is a pharmaceutical composition useful as an analgesic, diuretic, antiinflammatory, neuroprotection or psychotherapeutic agent which comprises a therapeutically effective amount of a compound of formula I in combination with a pharmaceutically acceptable carrier.

Yet another aspect of the present invention is a method for alleviating pain in a mammal which comprises administering to a mammal a composition as described above in unit dosage form.

Still another aspect of the present invention is a process for the preparation of a compound of formula I described below.

DETAILED DESCRIPTION

The present invention is a novel series of 1,2-cyclohexylaminoaryl amides of formula I

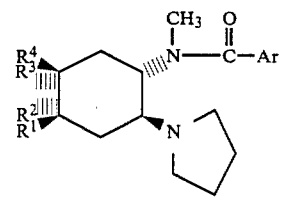

I and the pharmaceutically acceptable acid addition salts thereof wherein Ar, $R^1$, $R^2$, $R^3$, and $R^4$ are as described above.

The compounds of the present invention include solvates, hydrates, and pharmaceutically acceptable acid addition salts of the basic compounds of formula I above.

The term alkyl is a group of from one to six carbon atoms unless otherwise specified. This includes straight or branched groups such as methyl, ethyl, n-propyl, isopropyl, n-butyl, isobutyl, n-pentyl, and the like.

By virtue of the basic nitrogen on the cyclohexane moiety, pharmaceutically acceptable salts of compounds of the present invention may be prepared by reaction with appropriate acids. Suitable acids for the formation of pharmaceutically acceptable salts of the compounds of this invention form a class well known to practitioners of the pharmaceutical formulation arts (cf. S. M. Berge, et al., "Pharmaceutical Salts" in *J. Pharm. Sci.*, 66:1-19 (1977)), and include such acids as hydrochloric, hydrobromic, hydriodic, sulfuric, nitric, phosphoric, acetic, benzoic, citric, maleic, tartaric, succinic, gluconic, ascorbic, sulphamic, oxalic, pamoic, methanesulfonic, benzenesulfonic, ethanesulfonic, hydroxyethanesulfonic, and related acids and mixtures thereof.

The salts are generally prepared by reacting the free base with one equivalent of the desired acid in an appropriate unreactive solvent, followed by collection of the salt by filtration or recovery upon removal of the solvent. The free base may be regenerated, if desired, by reaction of the salt with one equivalent of a base such as sodium hydroxide, sodium bicarbonate, sodium carbonate, and the like. The salts may differ from the free base form of compounds of this invention in properties such as melting point and solubility in polar solvents, but are otherwise considered equivalent for the purposes of this invention.

Compounds of the present invention contain one or more asymmetric carbon atoms and exist in various stereo- and regio-isomeric forms. The present invention contemplates all stereo- and regio-isomeric forms of formula I above. The (+), (−) and (±) forms are all contemplated by the instant invention.

The individual stereo compounds or enantiomers are obtained, if desired, from a mixture of different forms by known methods of resolution such as the formation of diastereomers followed by recrystallization.

Compounds of the present invention are prepared by reacting an appropriate substituted cyclohexyldiamine of formula

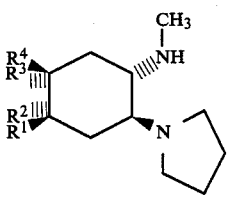   II with an activated carboxylic acid

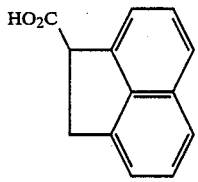   Ia

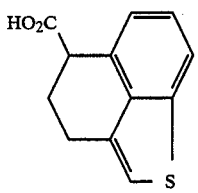   Ib

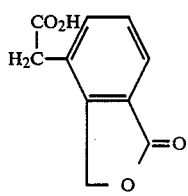   Ic

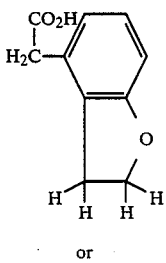   Id or

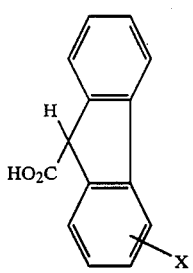   Ie or a reactive derivative formed from such a carboxylic acid.

First an aryl carboxylic acid is converted to the corresponding acid halide by reaction with thionyl halide. The appropriate diamine is dissolved in a suitable solvent such as dichloromethane at low temperature. Then equimolar amounts of the acid halide and the diamine are reacted to form a compound of formula I. This is recovered by precipitation from the mixed solvent. The product can be separated into diastereomers by known means.

Compounds of the present invention wherein the aryl is

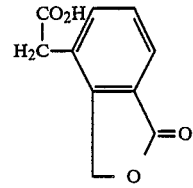   Ic or

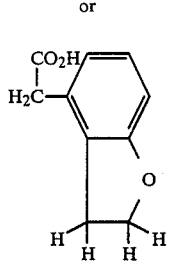   Id are prepared by converting the aryl carboxylic acid into the corresponding imidazole derivative by reaction with carbonyldiimidazole. The appropriate diamine is dissolved in a suitable solvent such as dichloromethane at low temperature. Then the imidazole derivative and the diamines are reacted. The reaction mixture is quenched with water and the aqueous layer is extracted with dichloromethane.

The novel compounds of the present invention have a very high kappa opioid affinity and selectivity and potency. For example, compound Ie $K_i=0.18$ nM with $\mu$/kappa ratio of 1416 and efficacy on rat paw pressure assay better than any known compound to the inventors with $MPE_{50}$ 0.014 mg/kg (IV) and 0.28 mg/kg (PO).

The compounds of the present invention possess significant analgesic activity with the potential for minimum dependence liability due to their selective kappa opioid receptor properties. In addition to acting as analgesics, selective kappa opioid agonists also cause opioid receptor-mediated sedation, diuresis, and corticosteroid elevations. Accordingly, the compounds of the present invention may also be useful diuretics, antiinflammatories and psychotherapeutic agents as well as analgesics.

The compounds of the present invention also have application in congestive heart failure, advanced hepatic cirrhosis, nephrotic syndrome, chronic renal failure, trauma associated with surgery, emotional and physical stress, endocrine disorders, syndrome of inappropriate antidiuretic hormone secretion and therapy with certain pharmacologic drug agents such as certain sulfonyl ureas, clofibrate, certain tricyclics such as carbamazipine, amitriptyline, thiothixene, flubenazine and thioridazine, certain antineoplastic agents, certain analgesics, and certain natriuretic diuretics.

The compounds of the present invention also have neuroprotective indications. As such, they are useful in the treatment of stroke and the treatment of cerebral ischemia (P. F. Vonvoightlander in *Brain Research*, 435:174–180 (1987)) and A. H. Tang, et al. in *Brain Research*, 403:52–57 (1987).

Representative examples of the compounds of this invention have shown activity in standard laboratory analgesic tests such as the rat paw pressure test as shown by the data appearing in Table 1 (M. B. Tyers, Brit. J. Pharmacol., (1980), 69, 503–512.

Moreover, representative examples of compounds of the present invention when tested in vitro to determine the extent of opioid receptor were found to be selectively bound to the kappa opioid receptors with much lower binding to the mu opioid receptor sites. The benefits of this selectivity in binding to opioid receptor binding sites has been discussed above and is also described in M. B. Tyers, Br. J. Pharmacol., 69:503–512 (1980).

Measurement of the kappa opioid receptor binding activity of compounds of the present invention was made by the following method. Guinea pig brain homogenates were prepared fresh daily utilizing the method of Gillan, et al., Br. J. Pharmacol., 70:481–490 (1980).

The binding of tritiated etorphine to brain homogenates was measured in the presence of unlabeled competitors compounds of the present invention with 200 nanomolar D-alanine-D-leucine-enkephalin (acronym DADLE) and 200 nanomolar D-ala-MePheGly-ol-enkephalin (acronym DAGO) added to saturate the delta and mu opioid receptors, respectively. The reaction was terminated by rapid filtration and the radioactivity bound to the filters counted by liquid scintillation spectrophotometry.

Measurement of the mu and delta opioid receptor binding activity of the compounds of this invention was made by the following method. Guinea pig brain homogenates were freshly prepared daily by the method of Gillan, et al., cited above.

Homogenates were incubated for 150 minutes at 0° C. with either tritiated DAGO to measure mu receptor binding activity, or with tritiated DADLE in the presence of a tenfold excess of unlabeled DAGO to measure delta opioid receptor binding. Nonspecific binding was determined in the presence of $10^{-6}$ molar DAGO and $10^{-6}$ molar DADLE.

Reactions were terminated by rapid filtration and the radioactivity bound to the filters counted by liquid scintillation spectrophotometry.

The data were analyzed by the methods of Scatchard, Ann. N.Y. Acad. Sci., 51:660–672 (1949) and Hill, J. Physiol., 40:IV–VIII (1910). The inhibition of the binding of tritiated etorphine, DAGO and DADLE by cold ligands was determined from the regression of log percentage inhibition of specific binding or log concentration of cold ligand. The inhibition constant, $K_i$, was calculated from the equation:

$$K_i = \frac{IC_{50}}{1 + [L]/K_D}$$

where [L] is the concentration of the labeled ligand and $K_D$ is the equilibrium dissociation constant.

The results of these tests are presented in Table 1.

TABLE 1

| Compound Number | | Opioid Binding $k_i$ nM | | | Rat Paw Pressure | |
|---|---|---|---|---|---|---|
| | | kappa | mu | mu/k | MPE$_{50}$ IV | (mg/kg) PO |
| 1a | (isomer I) | 16.3 | 2630 | 161 | | |
| 1b | (isomer II) | 31 | 387 | 12.5 | | |
| 1c | (isomer I) | 4.5 | 578 | 128 | | |
| 1e | (isomer I) | 0.18 | 255 | 1416 | 0.14 | 0.28 |

TABLE 1-continued

| Compound Number | | Opioid Binding $k_i$ nM | | | Rat Paw Pressure | |
|---|---|---|---|---|---|---|
| | | kappa | mu | mu/k | MPE$_{50}$ IV | (mg/kg) PO |
| 1f | (isomer II) | 1.2 | 273 | 227 | | |
| 1d | (isomer II) | 10.5 | 307 | 29 | | |
| 3d | | 9.7 | 4930 | 508 | 0.71 | |
| 2a | | 0.73 | 653 | 120 | 0.1 | |
| 3c | | 5.3 | 2870 | 541 | 0.1 | |

$k_i$ values represent the mean from concentration-response curves performed in triplicate from each of at least two separate experiments.
MPE$_{50}$ values represent the dose required to produce 50% of the maximum possible analgesic effect. They are derived from a single experiment with six animals per dose level.

The compounds of the present invention and/or their nontoxic, pharmaceutically acceptable acid addition salts may be administered to mammals in pharmaceutical compositions which comprise one or more compounds of this invention and/or salts thereof in combination with a pharmaceutically acceptable nontoxic carrier.

As parenteral compositions, the compounds of this invention may be administered with conventional injectable liquid carriers such as sterile, pyrogen-free water, sterile, peroxide-free ethyl oleate, dehydrated alcohols, polypropylene glycol, and mixtures thereof.

Suitable pharmaceutical adjuvants for the injectable solutions include stabilizing agents, solubilizing agents, buffers, and viscosity regulators. Examples of these adjuvants include ethanol, ethylenediamine tetraacetic acid (EDTA), tartrate buffers, citrate buffers, and high molecular weight polyethylene oxide viscosity regulators. These pharmaceutical formulations may be injected intramuscularly, intraperitoneally, or intravenously.

As solid or liquid pharmaceutical compositions, the compounds of the present invention may be administered to mammals orally in combination with conventional compatible carriers in solid or liquid form. These orally administered pharmaceutical compositions may contain conventional ingredients such as binding agents such as syrups, acacia, gelatin, sorbitol, tragacanth, polyvinylpyrrolidone, and mixtures thereof.

The compositions may further include fillers such as lactose, mannitol, starch, calcium phosphate, sorbitol, methylcellulose, and mixtures thereof.

These oral compositions may also contain lubricants such as magnesium stearate, high molecular weight polymers such as polyethylene glycol, high molecular weight fatty acids such as stearic acid, silica, or agents to facilitate disintegration of the solid formulation such as starch, and wetting agents such as sodium lauryl sulfate.

The oral pharmaceutical compositions may take any convenient form such as tablets, capsules, lozenges, aqueous or oily suspensions, emulsions, or even dry powders which may be reconstituted with water or other suitable liquids prior to use.

The solid or liquid forms may contain flavorants, sweeteners, and/or preservatives such as alkyl p-hydroxybenzoates. The liquid forms may further contain suspending agents such as sorbitol, glucose, or other sugar syrups, methyl-, hydroxymethyl-, or carboxymethylcellulose, and gelatin, emulsifying agents such as lecithin or sorbitol monooleate, and conventional thickening agents. The liquid compositions may be encapsulated in, for example, gelatin capsules.

As topically administered pharmaceutical compositions, the compounds of the present invention may be administered in the form of ointments or creams containing from about 0.1% to about 10% by weight of the active component in a pharmaceutical ointment or cream base.

Compounds of the present invention may be rectally administered in the form of suppositories. For preparing suppositories, for example, a low-melting wax such as a mixture of fatty acid glycerides or cocoa butter is first melted and the active ingredient is dispersed homogenously in the melt. The mixture is then poured into convenient sized molds and allowed to cool and solidify.

Preferably the pharmaceutical compositions of this invention are in unit dosage form. In such form, the preparation is subdivided into unit doses containing appropriate amounts of the active component. The unit dosage can be a packaged preparation with the package containing discrete quantities of the preparation. For example, the package may take the form of packaged tablets, capsules, and powders in envelopes, vials or ampoules. The unit dosage form can also be a capsule, cachet, or tablet itself or can be the appropriate number of any of these packaged forms.

The quantity of active compound in a unit dosage form may be varied or adjusted from about 0.01 mg to about 350 mg according to the particular application and the potency of the active ingredient.

When employed systematically in therapeutic use as analgesic agents in the pharmaceutical method of this invention, the compounds are administered at doses of from about 0.0001 mg to about 2.0 mg of active compound per kilogram of body weight of the recipient.

The following examples illustrate the present invention and are not intended to be in any way limiting.

EXAMPLE 1

Preparation of 1-Acenaphthenecarboxylic Acid

1-Acenaphthenecarboxylic acid was prepared by the method of Julia [*Bull. Chim. Soc. Fr.,* 1065 (1952)] or by the preferred, shorter route described below.

(i) 1-Tris(methylthio)methylacenaphthene

Acenaphthenol (35 g) was suspended in dry ether (200 ml) cooled to −5° C. with stirring and phosphorous tribromide (8 ml) added dropwise over five minutes to give a clear solution. The solution was allowed to warm to room temperature and stirred for a further two hours. The solution was washed with water and the ether layer dried over $NaCO_3$, reduced in volume at <40° C. in vacuo to 50 ml and cooled to 0° C.

Bright yellow crystals (of 1-bromoacenaphthene) were isolated by filtration and used, immediately, in the following step.

Tris(methylthio)methane (22 g) was dissolved in THF (100 ml) under $N_2$ at −78° C. 1.6 M BuLi in hexane solution (95 ml) was added slowly to yield a dense white precipitate. 1-Bromoacenaphthene (31.4 g) was dissolved in 20 ml of dry THF and added slowly to the above suspension to yield, after 10 minutes, a colorless solution. This was allowed to warm to room temperature, with the development of a brown color, and stirred overnight.

This solution was evaporated in vacuo to yield a brown oil (48 g). This material was crystallized from hexane to give orange crystals (29 g) of 1-(trismethylthio)methyl acenaphthene. m.p. 68°–70° C. Found: C, 62.62; H, 5.87; S, 31.11. Theory: C, 62.70; H, 5.92; S, 31.62.

(ii) Methyl 1-acenaphthenecarboxylate

1-Tris(methylthio)methyl acenaphthene (18.4 g), Mercury (II) Chloride (68 g) and Mercury (II) Oxide (22 g) were slurried in $MeOH/H_2O$, 12/1 (1500 ml), stirred at room temperature for 18 hours, then refluxed for two hours, and then allowed to cool.

The suspension was filtered and the cake washed with dichloromethane (2×100 ml). Water (1500 ml) was added to the solution and the total extracted with dichloromethane (2×1 L). The dichloromethane solution was washed with 75% aqueous ammmonium acetate (2×500 ml), dried over $MgSO_4$ and evaporated in vacuo to yield an orange oil (14 g). This was then purified by chromatography using hexane/ether 25/1 as eluent and Merck 15/11 silica gel as stationary phase to give a yellow liquid (10 g).

NMR 300 MHz, $CDCl_3$: δ 3.67 (dd) 1H, 3.78 (s) 3H, 3.91 (dd) 1H, 4.62 (dd) 1H, 7.35 (m) 1H, 7.5 (m) 3H, 7.7 (m) 2H.

(iii) 1-Acenaphthenecarboxylic acid

The above ester (1.9 g) was dissolved in 5 ml THF and this solution added to 6N KOH (40 ml). The mixture was refluxed for 10 hours and allowed to cool, then acidified with 5N HCl solution and extracted with ethyl acetate (3×50 ml). The extracts were combined, dried over $MgSO_4$ and evaporated in vacuo to yield a gummy orange solid (1.6 g). This was recrystallized form hexane/toluene 3/1 to yield orange crystals, mp 138°–145° C.

Scheme
Alternative Preferred Route to Acenaphthane Carboxylic Acid

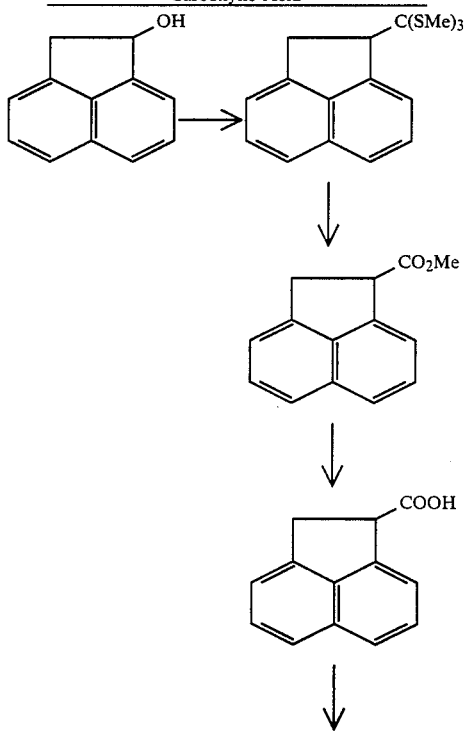

The acenaphthenecarboxylic acid (1.1 mmol) was stirred in neat thionyl chloride (5 ml) at reflux for one hour. The thionyl chloride was evaporated in vacuo and the resulting oil treated with 25 ml $CCl_4$. This mixture was then evaporated in vacuo to yield a brown oil which was used without further purification.

The appropriate diamine of structure II (1 mmol) was dissolved in a small volume (5 ml) of dichloromethane and cooled to 0° C. with stirring. The brown oil (above) was also dissolved in a similar volume of dichloromethane at room temperature and added to the acid solution dropwise. Stirring was continued for one hour at room temperature. The solution was then triturated with $Et_2O$ to yield a precipitate which was isolated by filtration.

This product was then separated into diastereoisomers (racemic pairs for Ia, Ib, Ic, Id and enantiomers for Ie and If using medium pressure silica gel chromatography (Merck 11695 15 μm silica, $CH_2Cl_2$/MeOH 10:1 eluant). The appropriate fractions were collected, evaporated in vacuo, dissolved in dichloromethane (5 ml). This solution was then treated with ethereal HCl and evaporated in vacuo to yield a white solid, recrystallized from isopropanol.

1.a. 1,2-dihydro-N-methyl-N-[-2-(1-pyrrolidinyl)cyclohexyl]-1-acenaphthylenecarboxamide, monohydrochloride (isomer I, mixture of (1α,2β) and (1β,2α) forms)

Elemental analysis for $C_{24}H_{30}N_2OHCl.0.4H_2O$ requires: Calcd: C, 71.00; H, 7,89; N, 6.90. Found: C, 71.01; H, 7.75; N, 6.92.

NMR 300 MHz ($DMSOd_6$) δ 1→2 (m) 12H, 3.20 (s) 3H, 3.30 (m) 4H, 3.48 (m) 1H, 3.65 (m) 1H, 3.78 (d of d) 1H, 4.55 (m) 1H, 5.02 (d of d) 1H, 7.4→7.6 (m) 5H.

mp >230° C.

IR (liquid film) 1641 $cm^{-1}$ NHCO; 3400 $cm^{-1}$ N+H.

1.b. 1,2-dihydro-N-methyl-N-[2-(1-pyrrolidinyl)cyclohexyl]-1-acenaphthylenecarboxamide, monohydrochloride (isomer II, mixture of (1α,2β) and (1β and 2α) forms)

Elemental analysis for $C_{24}H_{30}N_2OHCl.0.15H_2O$ requires: Calcd: C, 71.80; H, 7.85; N, 6.98. Found: C, 71.79; H, 7.84; N, 7.02.

NMR 300 MHz ($DMSOd_6$) δ 1→2 (m) 12H, 3.20 (m) and 3.32 (s) integral obscured, 3.69 (m) 4H, 4.55 (m) 1H, 5.02 (d of d) 1H, 7.22 (d) 1H, 7.32, 1H, 7.6 (m) 4H.

mp 228°-232° C.

IR (liquid film) 1641 $cm^{-1}$ NHCO; 3413 N+—H.

1.c. N-[4,5-dimethoxy-2-(1-pyrrolidinyl)cyclohexyl]-1,2-dihydro-N-methyl-1-acenaphthylenecarboxamide, monohydrochloride (isomer I, mixture of (1α,2β,4β,5β) and (1β,2α,4α,5α) forms)

Elemental analysis for $C_{26}H_{34}N_2O_3.HCl$ requires: Calcd: C, 68.03; H, 7.69; N, 6.10. Found: C, 67.88; H, 7.72; N, 6.07.

NMR 300 MHz ($DMSOd_6$) δ 1.5→2.2 (m) 8H, 3.1 (m) 1H, 3.18 (s) 3H, 3.30 (m) and 3.30 (s) and 3.35 (s) Integral obscured, 3.50 (m) 1H, 3.75 (m) 3H, 4.30 (m) 1H, 5.02 (d of d) 1H, 7.22 (d) 1H, 7.55 (m) 5H.

mp 137°-140° C.

IR liquid film 1637 $cm^{-1}$; NHCO 3402 $cm^{-1}$ N+—H.

1.d. N-[4,5-dimethoxy-2-(1-pyrrolidinyl)cyclohexyl]-1,2-dihydro-N-methyl-1-acenaphthylenecarboxamide, monohydrochloride (isomer II, mixture of (1α,2β,4β,5β) and (1β,2α,4α,5α) forms)

Elemental analysis for $C_{26}H_{34}N_2O_3HCl.H_2O$ requires: Calcd: C, 65.46; H, 7.82; N, 5.87. Found: C, 65.47; H, 7.82; N, 5.90.

NMR 300 MHz ($DMSOd_6$) δ 1.5 →2.2 (m) 8H, 3.1 (m) 1H, 3.28 (s) and 3.30 (s) and 3.33 (s) and 3.50 (m) Integral obscured, 3.80 (m) 3H, 4.80 (m) 1H, 5.02 (d of d) 1H, 7.22 (d) 1H, 7.31 (d) 1H, 7.61 (m) 4H.

mp 126°-133° C.

IR Liquid film 1636 $cm^{-1}$ NHCO; 3392 $cm^{-1}$ N+—H.

1.e. 1,2-dihydro-N-methyl-N-[7-(1-pyrrolidinyl)-1-oxaspiro[4.5]dec-8-yl]-1-acenaphthylenecarboxamide, monohydrochloride (isomer I, (5α,7α,8β) form)

Elemental analysis for $C_{27}H_{34}N_2O_2HCl.0.5H_2O$ requires: Calcd: C, 69.88; H, 7.81; N, 6.03. Found: C, 69.84; H, 7.77; N, 5.94.

NMR 300 MHz ($DMSOd_6$) δ1.5 →2 (m) 14H, 3.18 (s) 3H, 3.25 (m) Integral obscured 3.52 (m) 1H, 3.75 (m) 5H, 4.52 (m) 1H, 5.02 (d of d) 1H, 7.25 (d) 1H, 7.55 (m) 5H.

mp 143°-146° C.

$[α]_D20= +13.9°$, C =0.17, $CH_2Cl_2$.

IR Liquid film 1640 $cm^{-1}$; NHCO 3392 $cm^{-1}$ N+H.

1.f. 1,2-dihydro-N-methyl-N-[7-(1-pyrrolidinyl)-1-oxaspiro[4.5]dec-8-yl]-1-acenaphthylenecarboxamide, monohydrochloride (isomer II, (5α,7α,8β) form)

Elemental analysis for $C_{27}H_{34}N_2O_2HCl.1.3H_2O$ requires: Calcd: C, 67.77; H, 7.92; N, 5.84. Found: C, 67.50; H, 8.17; N, 5.48.

NMR 300 MHz ($DMSOd_6$) δ 1.5→2.1 (m) 14H, 3.20 (s) and 3.4→3.8 (m) Integral obscured, 4.55 (m) 1H, 5.02 (d of d) 1H, 7.21 (d) 1H, 7.32 (d) 1H, 7.55 (m) 4H.

mp 138°-140° C.

$[α]_D20= +43.5$ C=0.54, $CH_2Cl_2$.

IR Liquid film 1641 $cm^{-1}$;NHCO; 3398 $cm^{-1}$ N+—H.

EXAMPLE 2

The 9-fluorenyl carboxylic acid (1.1 mmol) was stirred in neat thionyl chloride at reflux for one hour. The thionyl chloride was evaporated in vacuo and the resulting oil treated with carbon tetrachloride (25 ml). This mixture was then evaporated in vacuo to yield a brown oil (not isolated).

The spiroether diamine (1 mmol) was dissolved in a small volume (5 ml) of dichloromethane at 0° C. with stirring. The acid chloride from above was dissolved in a similar volume of dichloromethane and this solution added to the amine solution dropwise.

Stirring was continued for one hour at room temperature, after which time the solution was triturated with $H_2O$ to yield an off-white precipitate. Recrystallized from propan-2-ol to yield white solid.

2.a. (−)-(5α,7α,8β)-N-methyl-N-[7-(1-pyrrolidinyl)-1-oxaspiro[4.5]dec-8-yl]-9H-fluorene-9-carboxamide, monohydrochloride Elemental analysis for $C_{28}H_{34}N_2O_2HCl.0.7H_2O$ requires: Calcd: C, 70.06; H, 7.51; N, 5.79. Found: C, 70.06; H, 7.65; N, 5.84.

NMR 300 MHz ($DMSOd_6$) δ 1.5 →2.1 (m) 14H, 3.1 →3.8 (m) +3.32 (s) Integral obscured, 4.55 (broad m) 1H, 5.49 (s) 1H, 7.35 (m) and 790 (m) 8H.

mp 201°-203° C.

IR (liquid film) 1641 $cm^{-1}$; NHCO 3401 N+—H.

2.b. (±)-trans-N-methyl-N-[2-(1-pyrrolidinyl)cyclohexyl]-9H-fluorene-9-carboxamide, monohydrochloride Elemental analysis for $C_{25}H_{30}N_2O.HCl$ 1.4$H_2O$ requires: Calcd: C, 68.73; H, 7.81; N, 6.41. Found: C, 68.73; H, 7.93; N, 6.25.

mp 243°-252° (iPrOH) (white microcrystalline solid).

IR (neat) 3416, 1641 $cm^{-1}$.

Mass Spec: (EI) m/e 374 ($M^+$, 5%) 151 (100%).

NMR δ (DMSOd6) 300 MHz 10.24 (1H, br, s), 7.95 (3H, m), 7.35 (5H, m), 5.45 (1H, s), 4.58 (1H, m), 3.72 (1H, m), 3.47 (3H, s), 3.35 (4H, m), 2.2-1.22 (12H).

EXAMPLE 3

4-Isobenzofuran-1-one acetic acid (1 mmol) and carbonyldiimidazole (1.1 mmol) were stirred under reflux in THF (10 ml) for one hour. The THF was then evaporated in vacuo and the residual oil dissolved in a small volume of dichloromethane (25 ml).

The diamine was dissolved in a similar small volume of dichloromethane (25 ml), cooled to 0° C. and the above solution added dropwise to it, with stirring. The resulting mixture was stirred at room temperature for a further two hours and then quenched with water. The aqueous layer was extracted with dichloromethane (3×100 ml), the extracts combined, washed with water, dried over MgSO4, and evaporated in vacuo.

The resulting oil was chromatographed using Merck Silica Gel Art 11695, CH2Cl2/MeOH 10:1 on a medium pressure preparative system.

The appropriate fractions were evaporated, the residual oil dissolved in 5 ml of dichloromethane and treated with ethereal HCl to yield a crystalline white material which was recrystallized from propan-2-ol.

3a. (±)-trans-1,3-dihydro-N-methyl-1-oxo-N-[2-(1-pyrrolidinyl)cyclohexyl]-4-isobenzofuranacetamide, monohydrochloride Elemental analysis for $C_{21}H_{28}N_2O_3 \cdot HCl \cdot 0.3H_2O$ requires: Calcd: C, 63.32; H, 7.49; N, 7.03. Found: C, 63.33; H, 7.37; N, 7.01.

NMR 300 MHz (DMSOd6) δ 1.2 →2.0 (m) 12H, 3.05 (s) 3H, 3.55 (m) 2H, 3.74 (d) 1H, 4.20 (d) 1H, 4.55 (broad m) 1H, 5.37 (d) 1H, 5.42 (d) 1H, 7.53 (t) 1H, 7.63 (d) 1H, 7.72 (d) 1H.

mp 251°–254° C.

IR (liquid film) 1645 cm$^{-1}$; NHCO, 1745 cm$^{-1}$; OCO, 3362 cm$^{-1}$, N+H.

3.b. (±)-(1α,2β,4β,5β)-N-[4,5-dimethoxy-2-(1-pyrrolidinyl)cyclohexyl]-1,3-dihydro-N-methyl-1-oxo-4-isobenzofuranacetamide mixture of (1α,2β,4β,5β) and (1β,2α,4α,5α) forms)

Elemental analysis for $C_{23}H_{32}N_2O_5HCl$ requires: Calcd: C, 60.99; H, 7.34; N, 6.18. Found: C, 60.75; H, 7.41; N, 6.20.

NMR 300 MHz (DMSOd6) δ 1.6 →2.0 (m) 8H, 3.05 (s) and 3.10 (m) 4H, 3.35 (m) and 3.31 (s) and 3.33 (s) 3.35 (m) Integral obscured, 3.52 (m) 1H, 3.75 (m) 2H, 3.82 (d) 1H, 4.24 (d) 1H, 4.80 (broad m) 1H, 5.38 (d) 1H, 7.52 (t) 1H, 7.62 (d) 1H, 7.71 (d) 1H.

mp 250°–252° C.

IR (liquid film) 1646 cm$^{-1}$; NHCO; 1757 cm$^{-1}$; COO; 3419 cm$^{-1}$ N+H.

3.c. (−)-(5α,7α,8β)-1,3-dihydro-N-methyl-1-oxo-N-[7-(1-pyrrolidinyl)-1-oxaspiro[4.5]dec-8-yl]-4-isobenzofuranacetamide monohydrochloride Elemental analysis for $C_{24}H_{32}N_2O_4 \cdot HCl \cdot H_2O$ requires: Calcd: C, 61.73; H, 7.55; N, 6.00; Cl, 7.59. Found: C, 61.99; H, 7.52; N, 5.91; Cl, 7.38.

NMR 300 MHz (DMSOd6) δ 1.5 →2.0 (m) 14H, 3.05 (s) 3H, 3.2→3.6 (m) Integral obscured, 3.86 (d) 1H, 4.19 (d) 1H, 4.58 (broad m) 1H, 5.35 (d) 1H, 5.43 (d) 1H, 7.55 (t) 1H, 7.66 (d) 1H, 7.75 (d) 1 H.

mp 182°–184° C.

IR (liquid film) 1645 cm$^{-1}$ NHCO; 1757 cm$^{-1}$; OCO. 3425 cm$^{-1}$ N+H.

$[\alpha]_D^{20} = -1.71$ C =0.5 CH2Cl2.

3.d. (−)-(5α,7α,8β)-2,3-dihydro-N-methyl-N-[7-(1-pyrrolidinyl)-1-oxaspiro[4.5]dec-8-yl]-4-benzofuranacetamide monohydrochloride IR max: 1646 (s), 1597 cm$^{-1}$.

$[\alpha]_D = -20°$, ε=0.64 (CH2Cl2).

EXAMPLE 4

A method for preparing the diamine intermediates to 1,2-dihydro-N-[4-methoxy-2-(1-pyrrolidinyl)cyclohexyl]-N-methyl-1-acenaphthylenecarboxamide monohydrochloride (isomers I and II, mixtures of (1α,2β,4α) forms), and 1,2-dihydro-N-[4-methoxy-2-(1-pyrrolidinyl)cyclohexyl]-N-methyl-1-acenaphthylenecarboxamide, monohydrochloride (isomers I and II, mixtures of (1α,2β,4β) forms).

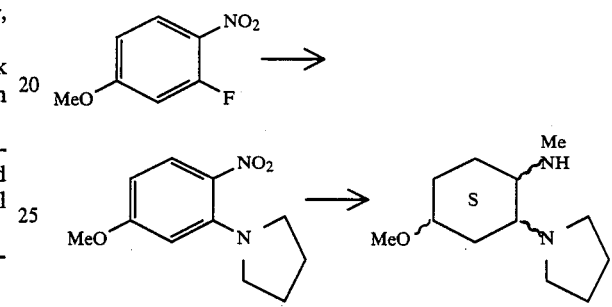

3-Fluoro-4-nitroanisole

3-Fluoro-4-nitrophenol (Fluorochem) (10 g, 64 mmol) was dissolved in butan-2-one (60 ml) and treated with potassium carbonate 16.6 g (120 mmol) at 40° C. for 10 minutes. The resulting suspension was cooled to 0° C., treated with methyl iodide (7.5 ml, 120 mmol), heated to 40° C. for three hours and concentrated in vacuo to 20 ml. The mixture was poured into dichloromethane (35 ml), filtered and the filtrate evaporated to give 3-fluoro-4-nitroanisole, as a white solid (8.0 g, 73%). An analytically pure sample was obtained by recrystallization from aqueous ethanol (4:1); mp 47°–49° C.; ir 1608 cm$^{-1}$.

3-(1-Pyrrolidinyl)-4-nitroanisole

3-Fluoro-4-nitroanisole (8.0 g, 47 mmol) was added over 10 minutes to pyrrolidine (25 ml) at room temperature. The resulting mixture was poured into dilute aqueous sodium hydroxide (100 ml) and extracted with dichloromethane (4×50 ml) to give an orange solid (7.5 g) which was purified by silica gel chromatography (CH2Cl2 eluant) to give 3-(1-pyrrolidinyl)-4-nitroanisole as an orange solid (5.2 g, 50%), mp 46°–48.5°; ir 1613, 1569 cm$^{-1}$.

Hydrogenation of 3-pyrrolidinyl-4-nitroanisole 3-(1-Pyrrolidinyl)-4-nitroanisole (0.50 g, 2.2 mmol), 5% rhodium on alumina (0.40 g), isopropyl alcohol (75 ml) and 48 wt percent aqueous fluoroboric acid (80 mg) were treated with hydrogen at 1000 psi and 80° C. for eight hours. The resulting mixture was filtered, concentrated in vacuo, dissolved in ethyl formate (5 ml) and triethylamine (1 ml) and heated to reflux for 50 minutes. The mixture was concentrated in vacuo and the residue dissolved in tetrahydrofuran (5 ml) then treated with a 1.0M solution of lithium aluminum hydride in diethyl ether (4 ml) at 30°–40° C. for 12 hours. Aqueous sodium hydroxide (0.2 ml) was added and the resulting precipitate removed by filtration. The filtrate was evaporated to give an oil (0.9 g) which contains (±)-(1α,2α,4α)-4-methoxy-N-methyl-2-(1-pyrrolidinyl)cyclohexanamine, (±)-(1α,2α,4β)-4-methoxy-N-methyl-2-(1-pyrrolidinyl)cyclohexanamine, (±)-(1α,2β,4α)-4-methoxy-N-methyl-2-(1-pyrrolidinyl)cyclohexanamine, and (±)-(1α,2β,4β)-4-methoxy-N-methyl-2-(1-pyrrolidinyl)cyclohexanamine.

We claim:

1. A compound of formula

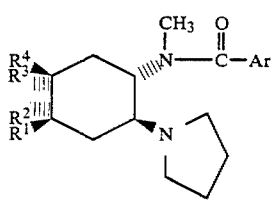

I and the pharmaceutically acceptable acid addition salts thereof
wherein $R_1$, $R_2$, $R_3$, $R_4$ = H; or
wherein one of $R_1$, $R_2$, $R_3$, $R_4$ may be =$OCH_3$ when the rest are all H; or
wherein $R_1 = R_4 = OCH_3$, and $R_2 = R_3 = H$;
Ar is

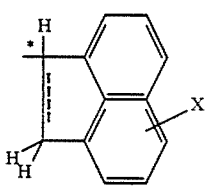

(a)

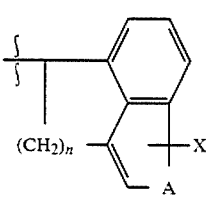

(b)

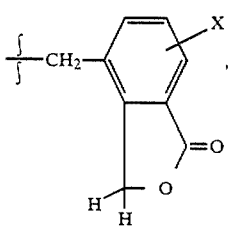

(c)

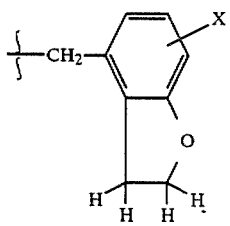

(d)

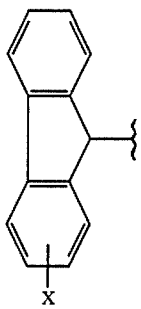

(e)

wherein X is hydrogen, fluorine, chlorine, alkyl of from one to six carbon atoms or aryl,
n is an integer from 2 to 4, and
A is oxygen or sulfur.

2. A compound according to claim 1 wherein $R^1$ $R^2$, $R^3$, and $R^4$ are hydrogen.

3. A compound according to claim 1 where one of $R^1$ $R^2$, $R^3$, or $R^4$ is $OCH_3$.

4. A compound according to claim 1 where $R^1$ and $R^4$ are both —$OCH_3$.

5. A compound according to claim 1 wherein Ar is

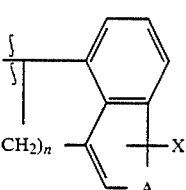

(a)

6. A compound according to claim 1 wherein Ar is

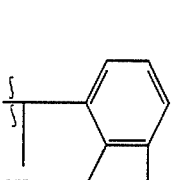

(b)

7. A compound according to claim 1 wherein Ar is

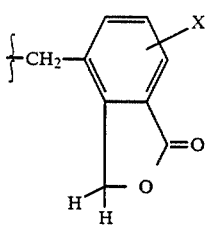

Ic or

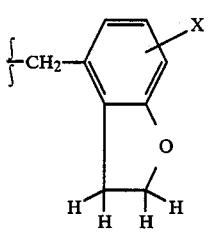

Id

8. A compound according to claim 1 wherein Ar is

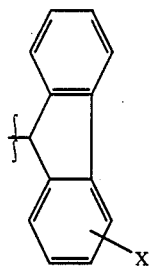

(e)

and R$_1$, R$_2$, R$_3$, and R$_4$ are hydrogen.

9. A compound according to claim 1 selected from the group consisting of:
1,2-dihydro-N-methyl-N-[2-(1-pyrrolidinyl)cyclohexyl]-1-acenaphthylenecarboxamide, monohydrochloride (isomer I, mixture of (1α,2β) and (1β,2α) forms),
1,2-dihydro-N-methyl-N-[2-(1-pyrrolidinyl)cyclohexyl]-1-acenaphthylenecarboxamide, monohydrochloride (isomer II, mixture of (1α,2β) and (1β,2α) forms),
N-[4,5-dimethoxy-2-(1-pyrrolidinyl)cyclohexyl]-1,2-dihydro-N-methyl-1-acenaphthylenecarboxamide, monohydrochloride (isomer I, mixture of (1α,2β,4β,5β) and (1β,2α,4α,5α) forms),
N-[4,5-dimethoxy-2-(1-pyrrolidinyl)cyclohexyl]-1,2-dihydro-N-methyl-1-acenaphthylenecarboxamide, monohydrochloride (isomer II, mixture of (1α,2β,4β,5β) and (1β,2α,4α,5α) forms),
1,2-dihydro-N-[4-methoxy-2-(1-pyrrolidinyl)cyclohexyl]-N-methyl-1-acenaphthylenecarboxamide, monohydrochloride (isomers I and II, mixtures of (1α,2β,4β) and (1β,2α,4α) forms),
1,2-dihydro-N-[4-methoxy-2-(1-pyrrolidinyl)cyclohexyl]-N-methyl-1-acenaphthylenecarboxamide, monohydrochloride (isomers I and II, mixtures of (1β,2α,4α) and (1α,2β,4β) forms).

10. A compound according to claim 1 selected from the group consisting of:
(±)-trans-N-methyl-N-[2-(1-pyrrolidinyl)cyclohexyl]-9H-fluorene-9-carboxamide, monohydrochloride.

11. A compound according to claim 1 selected from the group consisting of:
(±)-trans-1,3-dihydro-N-methyl-1-oxo-N-[2-(1-pyrrolidinyl)cyclohexyl]-4-isobenzofuranacetamide, monohydrochloride,
(±)-(1α,2β,4β,5β)-N-[4,5-dimethoxy-2-(1-pyrrolidinyl)cyclohexyl]1,3-dihydro-N-methyl-1-oxo-4-isobenzofuranacetamide.

12. A pharmaceutical composition useful for alleviating pain in a mammal comprising a therapeutically effective amount of a compound according to claim 1 in combination with a pharmaceutically acceptable carrier.

13. A method of alleviating pain in a mammal which comprises administering to said mammal a pharmaceutical composition which is a compound in accordance with claim 8 in unit dosage form.

14. A method for increasing urination in a mammal which comprises administering to said mammal a pharmaceutical composition which is a compound in accordance with claim 8 in unit dosage form.

15. A method for treating inflammation in a mammal which comprises administering to said mammal a pharmaceutical composition which is a compound in accordance with claim 8 in unit dosage form.

16. A method for treating psychotherapeutic disorders in a mammal which comprises administering to said mammal a pharmaceutical composition which is a compound in accordance with claim 8 in unit dosage form.

* * * * *